Dec. 11, 1956 D. B. COLE Plant Pat. 1,534
HONEY LOCUST TREE
Filed Dec. 6, 1955
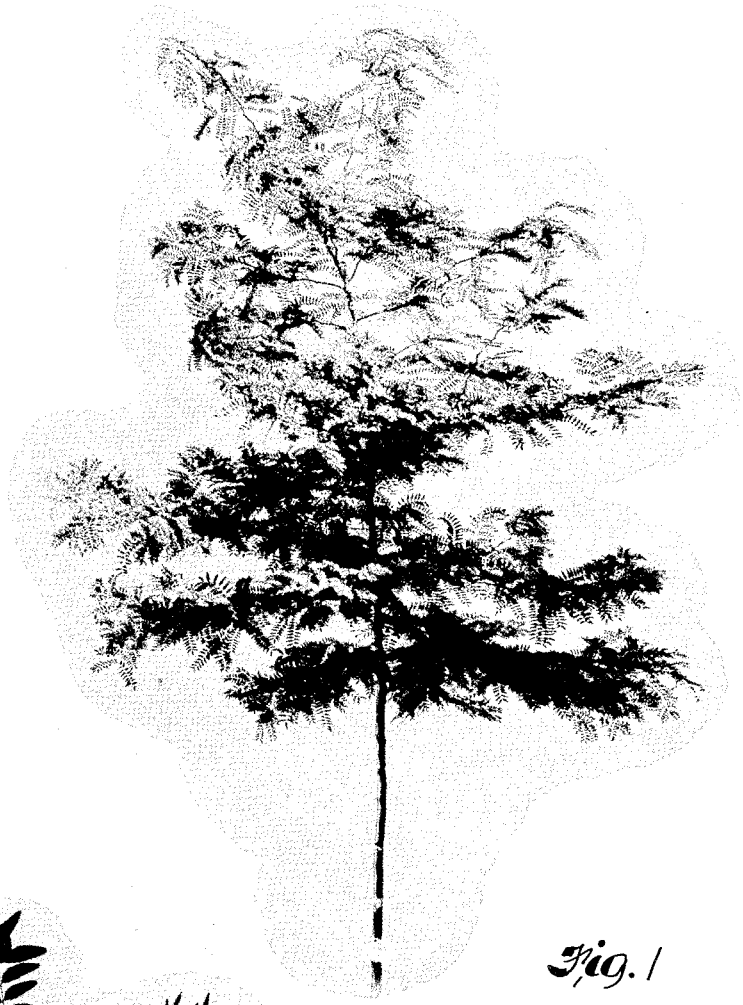
Fig. 1
Fig. 3
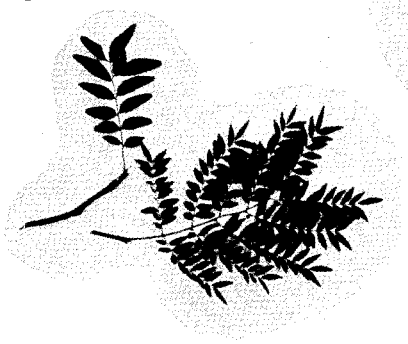
Fig. 2
INVENTOR.
DAVID B. COLE
BY
Oberlin & Limbach
ATTORNEYS.

United States Patent Office

Plant Pat. 1,534

Patented Dec. 11, 1956

1,534

HONEY LOCUST TREE

David B. Cole, Mentor Township, Lake County, Ohio, assignor to The Cole Nursery Company, Painesville, Ohio, a corporation of Ohio Application December 6, 1955, Serial No. 551,463

1 Claim. (Cl. 47—59)

The present invention relates to a new and distinct variety of honey locust tree originated by me, having novel habit of growth, and more particularly consists in a thornless and substantially seedless honey locust tree, *Gleditsia triacanthos* L., var. *inermis,* which retains its foliage for an unusually extended period.

My new honey locust tree grows with a strong, sturdy, straight trunk carrying well spaced and uniformly arranged branches. The rate of growth is medium vigorous, indicating a medium to large size tree at maturity, with a much more compact branching habit than is characteristic of the species. The branches and foliage form a well-shaped head with medium dark green leaflets.

The branches emerge from the trunk at a relatively wide angle assuring strong crotches. They are well spaced and radiate from the trunk in all directions, giving a well-shaped plant of exceptionally graceful growth habit. The bark on the early season's growth is uniformly dark green but late in the season the bark becomes a shiny, reddish brown color, often mottled somewhat with green. Lenticels are prominent. No thorns have been known to occur on this tree which appears to be absolutely thornless.

The mature leaves are 15 to 30 cm. long and both pinnate and bipinnate leaves are present. The leaves on the older current season's growth are mostly pinnate while those on wood formed later in the season are mostly bipinnate. The leaves are produced abundantly. The bipinnate leaves have from 8 to 16 pinnate, mostly 10 to 12. The leaf rachis is slightly grooved and is slightly hairy. The pinnate leaves have from 12 to 26, mostly 20 to 24, oblong-lanceolate to lanceolate leaflets, mostly 2½ to 3.0 cm. long, dark green on both sides, and slightly hairy below, occasionally glabrous. The leaflets are nearly entire, sometimes shallowly crenate toothed, and are closely spaced, the leaves being clustered on the older current season's growth and somewhat widely spaced on the younger wood. The foliage is medium dark green early in the season becoming very dark green at the latter part of the season and persists at least 10 days longer in the fall than those on the common thornless honey locust.

The flowers are substantially all male and extremely few fruits have been set. The flowers are borne in racemes.

Observation has shown that this tree has the ability to thrive in poorly drained, wet soil, a characteristic not common to most honey locusts.

I have propagated my new thornless substantially seedless honey locust tree at Painesville, Ohio, asexually by budding, and the tree can be very readily propagated in this manner, perpetuating all of its original character. The original parent specimen was a seedling grown by me at the same location. Such original parent specimen was discovered by me in a plantation of approximately 10,000 thornless honey locust seedlings grown by me from seed from selected parent trees exhibiting some tendency toward the desired characteristics.

In view of the fact that it is entirely thornless and substantially seedless, an unusual characteristic, and in view of its graceful and well-rounded form, straight erect growth, and fairly dense foliage, it is particularly well suited as a street and lawn tree. In common with other honey locusts, it is, of course, relatively immune to disease and insect pests. Its most striking and novel feature, however, which particularly enhances its use as a shade tree, is the fact that it retains its foliage in good condition for at least 10 days longer than any other honey locust presently known.

Referring now more particularly to the drawing:

Fig. 1 shows a specimen of my new thornless substantially seedless honey locust tree, several years of age, toward the end of the normal growing season;

Fig. 2 shows a bipinnate leaf illustrating the relatively dense growth of the leaflets; and Fig. 3 shows a pinnate leaf.

While the leaves, as above indicated, are of medium dark green color which is ordinarily considered highly desirable in an ornamental and shade tree, the color of the leaves is not so unusual as to be considered a feature distinguishing it from many common thornless honey locusts previously available.

I claim:

A new and distinct variety of thornless substantially seedless honey locust tree, *Gleditsia triacanthos* L., var. *inermis,* having a generally straight trunk, uniformly distributed well-spaced branches and fairly dense green foliage, particularly characterized in that such foliage remains green and in good condition for at least 10 days longer than the common thornless honey locust.

No references cited.